(12) United States Patent  (10) Patent No.: US 7,868,190 B2
Bhotla et al.  (45) Date of Patent: Jan. 11, 2011

(54) METHOD FOR PRODUCING PHENOLPHTHALEIN USING A HETEROPOLYACID CATALYST

(75) Inventors: Venkata Rama Narayanan Ganapathy Bhotla, Karnataka (IN); Shivappa Basappa Halligudi, Pune (IN); Gurram Kishan, Karnataka (IN); Salkod Parameshwar Mallika, Karnataka (IN); Bhaskar Veldurthy, Karnataka (IN)

(73) Assignee: Sabic Innovative Plastics IP B.V. (NL)

( * ) Notice: Subject to any disclaimer, the term of this patent is extended or adjusted under 35 U.S.C. 154(b) by 278 days.

(21) Appl. No.: 12/240,112

(22) Filed: Sep. 29, 2008

(65) Prior Publication Data

US 2010/0081829 A1 Apr. 1, 2010

(51) Int. Cl.
*C07D 307/78* (2006.01)
(52) U.S. Cl. ....................... 549/308
(58) Field of Classification Search .......... 549/308
See application file for complete search history.

(56) References Cited

U.S. PATENT DOCUMENTS 2,192,485 A * 3/1940 Hubacher ............. 549/308

(Continued)

FOREIGN PATENT DOCUMENTS

WO 2008/091368 A1 7/2008

OTHER PUBLICATIONS

Xue, Xun-yu (An improvement of the synthesis for phenolphthalein. Huaxue Shiji Biajinbu, 2006: 28(11); p. 697-698).*

(Continued)

*Primary Examiner*—Kamal A Saeed
*Assistant Examiner*—Valerie Rodriguez-Garcia
(74) *Attorney, Agent, or Firm*—Cantor Colburn LLP

(57) ABSTRACT

A method for producing a phenolphthalein compound comprises: reacting a phenolic compound of the formula:

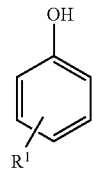

wherein $R^1$ is a hydrogen or a $C_1$-$C_{12}$ hydrocarbyl group, with a phthalic anhydride compound of the formula:

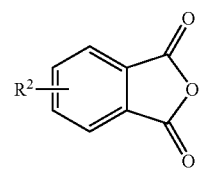

wherein $R^2$ is a hydrogen, a $C_1$-$C_{12}$ hydrocarbyl group, or a halogen, in the presence of a heterogeneous catalyst and a promoter to form a reaction mixture comprising a phenolphthalein compound of the formula:

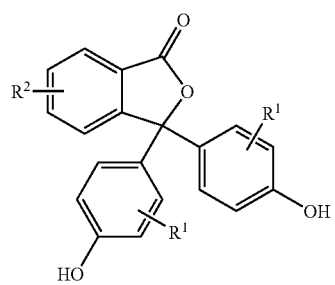

wherein each $R^1$ is independently a hydrogen or a $C_1$-$C_{12}$ hydrocarbyl group; and $R^2$ is a hydrogen, a $C_1$-$C_{12}$ hydrocarbyl group, or a halogen; wherein the heterogeneous catalyst comprises, on a porous support, a calcination product of a heteropolyacid composition.

20 Claims, 1 Drawing Sheet

U.S. PATENT DOCUMENTS

| | | | |
|---|---|---|---|
| 2,522,939 A | | 9/1950 | Gamrath |
| 2,522,940 A | | 9/1950 | Gamrath |
| 4,252,725 A | * | 2/1981 | Prindle et al. ............... 549/308 |
| 6,573,405 B1 | | 6/2003 | Abbott et al. |
| 7,041,774 B2 | | 5/2006 | Kishan et al. |
| 7,045,482 B2 | | 5/2006 | Chun et al. |
| 2006/0222601 A1 | * | 10/2006 | Sabnis et al. .................. 424/49 |
| 2008/0177091 A1 | * | 7/2008 | Basale et al. ................ 549/308 |

OTHER PUBLICATIONS

Hu, Shuxian (Preparation of phenolphthalein using sulfonic acid-type cation exchange resin as catalyst. Lizi Jiaohuan Yu Xifu, 1989: 5(6); p. 454-457).*

International Search Report for PCT/IB2009/054075, mailing date Apr. 9, 2010, 6 pages.

Written Opinion of International Search Report for PCT/IB2009/054075, mailing date Apr. 9, 2010, 6 pages.

International Search Report for PCT/IB2009/054170, mailing date Nov. 16, 2009, 6 pages.

Written Opinion of International Search Report for PCT/IB2009/054170, mailing date Nov. 16, 2009, 7 pages.

Yin, et al., "High Regioselective Diels-Alder Reaction of Myrcene with Acrolein Catalyzed by Zinc-Containing Ionic Liquids," Adv. Synth. Catal., 347, (2005) pp. 137-142.

Bordoloi, et al., "Liquid-phase Veratrole Acylation and Toluenme Alkylation Over WOx/ZrO2 Solid Acid Catalysts," Journal of Molecular Catalysis A: Chemcial, 247, (2006) pp. 58-64.

* cited by examiner

METHOD FOR PRODUCING PHENOLPHTHALEIN USING A HETEROPOLYACID CATALYST

BACKGROUND

This disclosure is directed to methods of manufacturing phenolphthalein compounds, in particular methods using a heteropolyacid catalyst.

Phenolphthalein compounds are useful as a starting material to make a wide range of products. For example, phenolphthalein compounds are important raw materials for the synthesis of 3,3-bis(4-hydroxyphenyl)phthalimidine and 2-hydrocarbyl-3,3-bis(4-hydroxyaryl)phthalimidines, in particular 2-phenyl-3,3-bis(4-hydroxyphenyl)phthalimidine (PPPBP). These phthalimidine compounds can be used in the manufacture of homopolycarbonates and copolycarbonates.

Phenolphthalein has been produced in a homogenous process in which phthalic anhydride is reacted with phenol in the presence of zinc chloride ($ZnCl_2$) as a catalyst. In U.S. Pat. No. 2,522,939, Gamrath disclosed improving this widely used process by the addition of chlorosulphonic acid as an activating agent (also referred to as a promoter) for the zinc chloride. This process has become commercially used because of the high purity, selectivity, and yield obtained.

Presently available manufacturing processes for phenolphthalein are time consuming and require large amounts of energy and chemicals, as well as complex equipment. U.S. patent application Ser. No. 11/626,671 discloses an improved method for producing and purifying phenolphthalein compounds on a commercial scale that requires fewer resources. In particular, after reacting a phthalic anhydride compound and a phenol compound in the presence of a catalyst and a promoter to form a reaction mixture comprising the phenolphthalein compound, the reaction mixture is treated with a solvent system to form a slurry. The slurry can then be filtered to obtain a solid material, which, after washing in water at an elevated temperature, comprises the phenolphthalein compounds in high purity. This commercial process, however, still employs zinc chloride and chlorosulphonic acid to catalyze the reaction.

There are several significant challenges associated with processes for manufacturing phenolphthalein using zinc chloride. In commercial practice, the zinc chloride is used in relatively large amounts, 0.6 mole of zinc chloride per mole of phthalic anhydride. The used catalyst must be separated from the reaction mixture after quenching of the reaction. The difficulty of separating the catalyst, which is used in slurry form, is increased because the slurry becomes very viscous over time. Importantly, the large amounts of used catalyst cannot be reused and must be disposed of safely.

Different approaches to making phenolphthalein have been employed both on a laboratory and commercial scale. For example, ion exchange resins are also known for phenolphthalein preparation, as disclosed in U.S. Pat. No. 4,252,725. However, commercial manufacture is very demanding in terms of yield, purity, and other characteristics. The use of zinc chloride in the preparation of phenolphthalein, despite its problems, remains the industry standard in the absence of a practical replacement.

It would be desirable to develop a process for the preparation of phenolphthalein compounds wherein the catalyst is more readily separated from the reaction mixture. It would further be desirable to develop a process for the preparation of phenolphthalein compounds that reduces waste generation, for example by allowing the catalyst to be reused. It would also be desirable if these processes provided phenolphthalein compounds in high purity.

BRIEF SUMMARY OF THE INVENTION

Some or all of the above-described deficiencies are addressed by a method for producing a phenolphthalein compound comprising: reacting a phenolic compound of the formula:

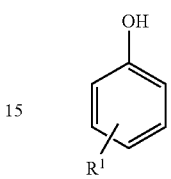

wherein $R^1$ is a hydrogen or a $C_1$-$C_{12}$ hydrocarbyl group, with a phthalic anhydride compound of the formula:

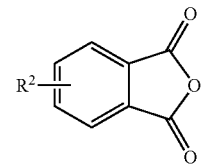

wherein $R^2$ is a hydrogen, a $C_1$-$C_{12}$ hydrocarbyl group, or a halogen, in the presence of a heterogeneous catalyst and a promoter to form a reaction mixture comprising a phenolphthalein compound of the formula:

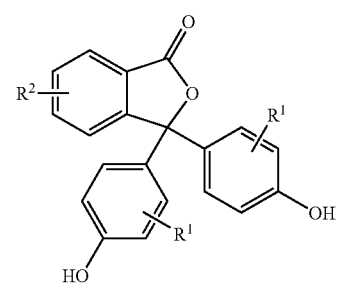

wherein each $R^1$ is independently a hydrogen or a $C_1$-$C_{12}$ hydrocarbyl group; and $R^2$ is a hydrogen, a $C_1$-$C_{12}$ hydrocarbyl group, or a halogen; wherein the heterogeneous catalyst comprises, on a porous support, a calcination product of a heteropolyacid composition.

In another embodiment, a method for producing a phenolphthalein compound comprises: reacting a phenolic compound of the formula:

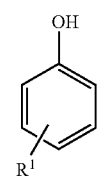

wherein $R^1$ is a hydrogen or a $C_1$-$C_{12}$ hydrocarbyl group, with a phthalic anhydride compound of the formula:

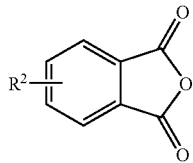

wherein $R^2$ is a hydrogen, a $C_1$-$C_{12}$ hydrocarbyl group, or a halogen, in the presence of a heterogeneous catalyst and a promoter to form a reaction mixture comprising a phenolphthalein compound of the formula:

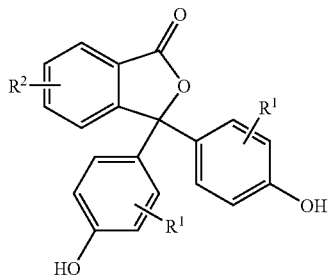

wherein each $R^1$ is independently a hydrogen or a $C_1$-$C_{12}$ hydrocarbyl group; and $R^2$ is a hydrogen, a $C_1$-$C_{12}$ hydrocarbyl group, or a halogen; wherein the heterogeneous catalyst comprises, on a porous support, a calcination product of an oxygen-containing inorganic heteropolyacid comprising a polyatom selected from the group consisting of molybdenum, tungsten, vanadium, niobium, or a combination thereof, and a central heteroatom selected from the group consisting of phosphorous, silicon, germanium, boron, cobalt, and a combination thereof.

In still another embodiment, a method for producing a phenolphthalein comprises: reacting a phenolic compound of the formula:

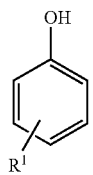

wherein $R^1$ is a hydrogen, with a phthalic anhydride compound of the formula:

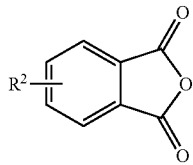

wherein $R^2$ is a hydrogen, a $C_1$-$C_{12}$ hydrocarbyl group, or a halogen, in the presence of a heterogeneous catalyst and a promoter to form a reaction mixture comprising a phenolphthalein compound of the formula:

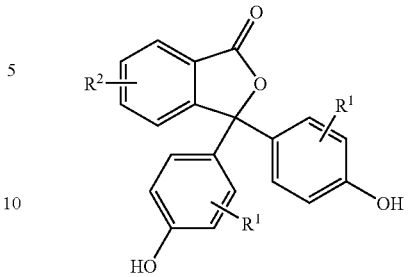

wherein each $R^1$ is a hydrogen, and $R^2$ is a hydrogen, a $C_1$-$C_{12}$ hydrocarbyl group, or a halogen; wherein the heterogeneous catalyst comprises, on a porous support, a calcination product of a heteropolyacid composition that comprises a compound, or structural units derived from the compound, of the formula:

$$(H)_n(M^4)(M^5)_{12}O_{40}$$

wherein the subscript n is 3 or 4, $M^4$ is phosphorus or silicon, and $M^5$ is tungsten, molybdenum, or a combination comprising at least one of the foregoing metals; quenching the reaction mixture comprising the phenolphthalein compound with a first organic solvent in which the phenolphthalein compound dissolves to provide a first quenched reaction mixture comprising dissolved phenolphthalein compound; filtering the first quenched reaction mixture to provide a solid residue comprising the heterogeneous catalyst and a filtrate comprising the organic solvent and the phenolphthalein compound; removing the organic solvent from the filtrate to provide a residue comprising the phenolphthalein compound; and regenerating the heterogeneous supported catalyst.

The manufacture of phthalimidines from the above-described phenolphthaleins is further disclosed.

These and other features, aspects, and advantages of the present invention will become better understood when the following detailed description is read with reference to the accompanying Figures.

DETAILED DESCRIPTION

Figure 1:
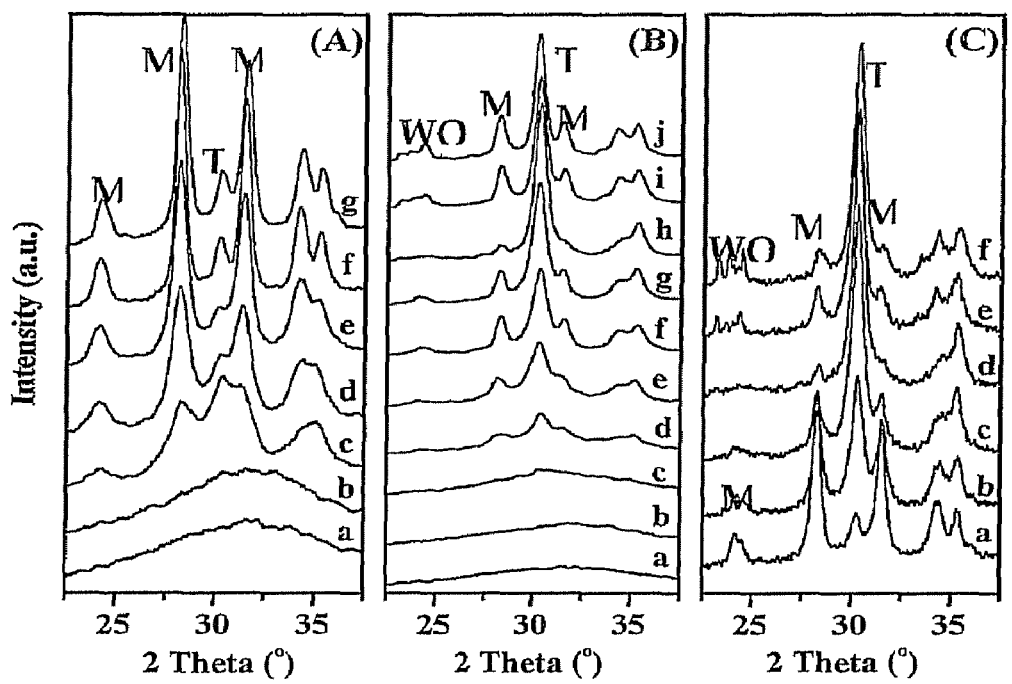
FIGS. 1A, 1B, and 1C show X-ray diffraction patterns, according to Example 3, for various supports with and without the use of a heteropolyacid composition.

The inventors hereof have discovered that use of specific supported heterogeneous catalysts in a process for the manufacture of phenolphthalein allows ready separation of the catalyst from the reaction mixture, thereby providing a more efficient and less wasteful process. It has further been found that the catalyst can be regenerated and reused, which again provides a more efficient and less wasteful process. In a still further advantage, use of the heterogeneous catalyst provides phenolphthalein compounds of high purity.

In one embodiment, the heterogeneous catalyst comprises a calcined product of a heteropolyacid composition on a porous support. A heteropolyacid is an oxygen-containing inorganic polyacid that contains molybdenum (Mo), tungsten (W), vanadium (V), niobium (Nb), and the like as a polyatom, and phosphorous (P), silicon (Si), germanium (Ge), boron (B), cobalt (Co), and the like as a central heteroatom. In one embodiment, a central phosphorous or silicon atom connects twelve peripheral octahedrally coordinated metal atoms. A "heteropolyacid composition" as used herein is inclusive of both the acid form and the corresponding salt, wherein one or more of the acidic hydrogens in the acid is replaced by a cation, for example an alkali metal, an alkaline earth metal, an ammonium ion, a $C_{1-8}$ tetraalkyl ammonium ion, and the like. A combination of cations can be used. More specifically, in one embodiment, the heterogeneous catalyst comprises a heteropolyacid composition containing molybdenum, tungsten, vanadium or combinations comprising at least one of the foregoing metals as the polyatom, and phosphorous or silicon as a central heteroatom. In one embodiment, mixtures of metals are employed in the heteropolyacid composition, for example, both a molybdenum and a tungsten metal. In another specific embodiment, the porous support is a mixture of a metal oxide with another material, for example, an aluminosilicate zeolite.

In particular embodiments, the catalyst is a heteropolyacid composition comprising a heteropolyacid (or the corresponding salt) of the formula:

$$(H)_n(M^4)(M^5)_{12}O_{40}$$

wherein n is 3, 4, 5, or 6, $M^4$ is phosphorus or silicon, and $M^5$ is tungsten, molybdenum, or a combination comprising at least one of the foregoing metals. When $M^4$ is phosphorus, n is 3 and when $M^4$ is silicon, n is 4. For example, the supported heterogeneous catalyst comprises at least one heteropolyacid composition comprising silicotungstic acid, tungstophosphoric acid, molybdophosphoric acid, and precursors thereof, or combinations comprising at least one of the foregoing heteropolyacids, or their corresponding salts. Heteropolyacids can include both tungsten and molybdenum, for example, molybdotungstophophoric acid ($H_3PMo_{12-x}W_xO_{40}$, wherein x is 1 to 12).

In a specific embodiment, the heteropolyacid composition comprises silicotungstic acid, silicomolybdic acid, tungstophosphoric acid, molybdophosphoric acid, or a combination comprising at least one of the foregoing acids, or their corresponding salts.

In another embodiment, the heteropolyacid includes other metals in addition to molybdenum or tungsten. In one embodiment, a heteropolyacid composition is of the formula:

$$(M^6)(M^7)(M^8)_{12}O_{40}$$

wherein $M^6$ is a Group III element (boron, aluminum, or the like); $M^7$ is phosphorus or silicon, and $M^8$ is tungsten or molybdenum.

In still another embodiment, the heteropolyacid is of the formula:

$$H_{3+n}(M^7)V_n(M^8)_{12-n}O_{40}$$

wherein n is 0 to 4, and $M^7$ and $M^8$ are as defined above. For example, such heteropolyacids can include 12-molybdotungstophosphoric acid ($H_{3+x}PMo_{12-x}W_xO_{40}$, wherein x is 0 to 12), 18-molybdovanadophosphoric acid ($H_{6+x}P_2Mo_{18-x}V_xO_{62}$, wherein x is 0 to 18), 18-tungstoniobiophosphoric acid, and the like.

A heteropolyacid and/or its salt can be purchased or prepared by known methods, for example, as disclosed in U.S. Pat. No. 7,045,482 or U.S. Pat. No. 6,956,134. Heteropolyacids are also commercially available from E-Merck, for example.

The metals in the calcined catalyst (calcined heteropolyacid composition) or in the support are not limited to any particular valence state. These metals can be present in the catalyst or support in any possible positive oxidation for the metal species. "Metal oxide" as used herein means compositions comprising the metal oxide, which may or may not further comprise the corresponding metal hydroxides and/or waters of hydration. Thus, a "metal oxide" refers qualitatively to compositions wherein an elemental analysis reveals the presence of the relevant metal (in one or more valence states) and oxygen. For example, an exemplary porous support disclosed herein is zirconia, having the formula $ZrO(OH)_x$. As is understood by those of skill in the art, the amount of oxygen measured in such an analysis will depend on a number of factors such as the valence state of the metal, for example a Group IVB or Group VIB metal, moisture content, and the like. For convenience, the porous supports can be referred to herein using formulas such as $XO_2$ wherein, for example, X is a Group IVB metal such as zirconium. It will be appreciated, however, that this notation is for convenience, and metal oxides as represented by $XO_2$ may comprise the corresponding hydroxides and/or contain waters of hydration. Thus, the heterogeneous catalysts described herein are not subject to a single specific formula for every embodiment.

Various porous materials that can be used as the support include, for example, zirconia (zirconium oxide, $ZrO_2$), titania (titanium oxide, $TiO_2$ (anatase or rutile)), ceria (cerium oxide, $CeO_2$), aluminosilicates, silica (silicon dioxide, $SiO_2$), alumina, (aluminum oxide, $Al_2O_3$ (acidic or neutral)), zinc oxide, magnesia (magnesium oxide, MgO), niobium oxide, tin oxide, and combinations comprising at least one or more of the foregoing materials. Aluminosilicates, for example, can include various zeolites such as the SBA series of zeolites, for example, SBA-11, SBA-12, and SBA-15. Other exemplary types of zeolites include mordenite, ZSM-5, L-zeolite, faujasite, ferrierite, and chabazite. In one specific embodiment, the support is zirconia.

In one specific embodiment, the heteropolyacid composition comprises tungsten and the porous support comprises zirconia. Specific embodiments include, for example, supported heterogeneous catalysts in which the heteropolyacid composition that is used and the porous support are, respectively, silicotungstic acid and zirconia, tungstophosphoric acid and zirconia, tungstophosphoric acid and titania, tungstophosphoric acid and both zirconia and aluminosilicate, and a combination comprising at least one of the foregoing pairs or groups of heteropolyacid composition and porous support.

In various embodiments, the porous support is a microporous or a mesoporous material. Mesoporous supports have a pore size of greater than or equal to about 10 to about 100 angstroms, and the microporous supports have a pore size of less than or equal to about 10 angstroms, as determined by BET measurements. The supported heterogeneous catalyst has a surface area of 100 to 750 m²/g, specifically 300 to 600 m²/g, measured in accordance with the BET method. The surface density of the tungsten or molybdenum (or both) in the supported heterogeneous catalyst is 0.1 to 5, specifically 1 to 2.5, atoms per nanometer square area, as determined according to the method of A Bordoloi et al, *Journal of Molecular Catalysis A; Chemical* 247 (2006) 58-64, page 60.

The surface density of the metal on the supported heterogeneous catalyst, expressed as the number of metal atoms per nanometer square meter (metal atoms per nm²) is calculated based on the heteropolyacid loading and surface area, using the equation:

Surface density of metal={[heteropolyacid loading wt. %/100]×6.023×10²³}/{(formula weight of heteropolyacid)×BET surface area (m²g/l×10¹⁸)}.

The supported heterogeneous catalysts are made by a variety of methods. In one embodiment, employing incipient wetness impregnation of a support or support precursor with a methanolic solution of the heteropolyacid compound, the catalyst is dispersed over the surface of the support or a support precursor, and the amounts are chosen so as to achieve the desired surface density. Thermal treatment of the catalyst and support is carried out to make the final supported heterogeneous catalyst.

In one embodiment, when using a zirconia support, the supported catalyst is made by wet impregnation of zirconium oxyhydroxide with a heteropolyacid composition. Zirconium oxyhydroxide is prepared by dissolving zirconium oxychloride in distilled water, after which sufficient aqueous ammonia is added to precipitate zirconium hydroxide. After the precipitate is separated, washed, and dried, the product is impregnated with a solution of the heteropolyacid. After removing excess water and drying in an oven, the dried material is calcined with heating to obtain the supported heterogeneous catalyst.

The surface area of the supported heterogeneous catalyst is influenced by both the support and catalyst. For example, it has been found that pure zirconium oxyhydroxide dried at 120° C. showed a surface area of about 330 m2 per gram. After calcination at 800° C., the surface area decreased to 10 m2 per gram. Addition of catalyst to the support can increase the surface area in some embodiments. Without wishing to be bound by theory, this might be explained by the catalyst interacting with the zirconia support to inhibit sintering and stabilizing the tetragonal phase of zirconia, which leads to an increase in surface area. However, higher loadings of catalyst can cause the formation of crystalline metal oxide such as tungsten oxide that can plug the pores and decrease the specific surface area.

In some embodiments, the X-ray diffraction (XRD) pattern of the supported catalysts showed that the presence of the heteropolyacid catalyst can influence the crystallization of zirconium oxyhydroxide into zirconia. Pure zirconia calcined at 750° C. is mainly monoclinic with only a small amount of the tetragonal phase. The tetragonal phase becomes dominant with about 15 weight percent (wt. %) heteropolyacid catalyst. For lesser amounts of heteropolyacid catalyst compositions, the XRD pattern is more of a sum of the monoclinic and tetragonal phases of zirconia. The tetragonal content of zirconia at a fixed loading depends on the calcination temperature. In one embodiment, the zirconia in the catalyst comprises greater than 10, up to 100 volume percent of tetragonal zirconia, specifically, 50 to 100 volume percent, more specifically 80 to 100 volume percent of tetragonal zirconia, all based on XRD analysis. At less than 25 wt. % heteropolyacid catalyst loading, and less than 850° C. calcination, no diffraction lines or only a slight indication can be attributed to crystalline WO₃ in bulk from tungsten-containing heteropolyacids. Without being bound by theory, this may indicate decreased dispersion of catalyst on the support.

In another embodiment, a supported heterogeneous catalyst is obtained by reacting a heteropolyacid composition with a functionalized zeolite composition, as disclosed, for example, in U.S. Pat. No. 7,041,774 B2. In one embodiment, a solution of the heteropolyacid in a suitable solvent is treated with a functionalized zeolite, for example, having sulphonic acid or mercapto groups, followed by evaporation of the solvent and calcination to furnish the heteropolyacid-functionalized zeolite. Suitable solvents used for reaction with the heteropolyacid include water and $C_1$ to $C_8$ alcohols, such as methanol, ethanol, isopropanol, and n-butanol. Thus, structural units of a heteropolyacid are covalently linked to a porous support.

The amount of heteropolyacid used in the heterogeneous catalyst varies, depending on the type of heteropolyacid, the type of support, the desired activity of the heterogeneous catalyst, and like consideration. For example, the total amount of the heteropolyacid is 5 to 70 wt. %, specifically 10 to 30 wt. %, based on the weight of the support.

The supported, heterogeneous catalysts are useful to catalyze the reaction of a phenolic compound and a phthalic anhydride compound to produce a phenolphthalein compound. The phenolic compound is of formula (I):

(I)

wherein $R^1$ is a hydrogen or $C_1$-$C_{12}$ hydrocarbyl group, specifically a hydrogen, $C_1$-$C_3$ alkyl, or $C_1$-$C_3$ alkoxy. In one embodiment, $R^1$ is a hydrogen.

The phthalic anhydride compound is of formula (II):

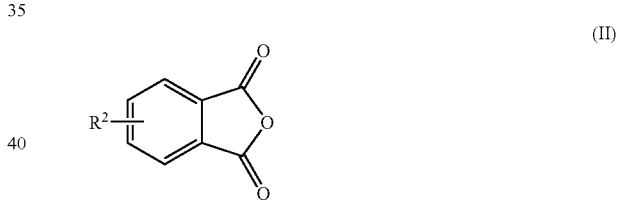

(II)

wherein $R^2$ is a hydrogen, a $C_1$-$C_{12}$ hydrocarbyl group, or a halogen, specifically a hydrogen, $C_1$-$C_3$ alkyl, $C_1$-$C_3$ alkoxy, bromine, or chlorine. In one embodiment, $R^2$ is a hydrogen.

The phenolphthalein compound produced in the reaction is of formula (III):

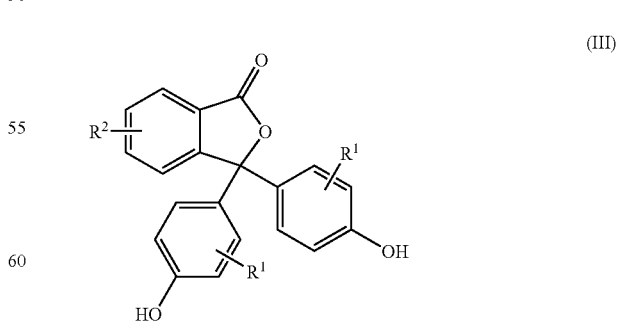

(III)

wherein each $R^1$ is independently a hydrogen or a $C_1$-$C_{12}$ hydrocarbyl group; and $R^2$ is a hydrogen, a $C_1$-$C_{12}$ hydrocarbyl group, or a halogen. In a specific embodiment, each $R^1$ is the same, and is a hydrogen, $C_1$-$C_3$ alkyl, or $C_1$-$C_3$ alkoxy; and $R^2$ is $C_1$-$C_3$ alkyl, $C_1$-$C_3$ alkoxy, bromine, or chlorine. In another embodiment, each $R^1$ is a hydrogen, and $R^2$ is a hydrogen.

The phenolic compound is reacted with the phthalic anhydride compound in the presence of the heterogeneous catalyst and a co-catalytically effective amount of a promoter. Exemplary promoters include chlorosulphonic acid, a $C_1$-$C_{12}$ alkyl sulphonic acid, a $C_6$-$C_{12}$ aryl sulphonic acid, a $C_1$-$C_{12}$ alkyl $C_6$-$C_{12}$ aryl sulphonic acid, a halogenated $C_1$-$C_{12}$ alkyl sulphonic acid, a halogenated $C_6$-$C_{12}$ aryl sulphonic acid, a halogenated $C_1$-$C_{12}$ alkyl $C_6$-$C_{12}$ aryl sulphonic acid, trichloroacetic acid, triflic acid, boron trifluoride, and combinations comprising at least one of the foregoing promoters. Specific promoters include chlorosulphonic acid, methanesulphonic acid, dodecylbenzenesulphonic acid, triflic acid, boron trifluoride, p-toluene sulphonyl chloride, and combinations comprising at least one of the foregoing. In one embodiment, the promoter is chlorosulphonic acid.

The reaction is typically carried out using a stoichiometric excess of the phenolic compound relative to the phthalic anhydride. In one embodiment, the reaction is carried out using a molar ratio of the phthalic anhydride compound to the phenolic compound of 1:2.1 to 1:10, specifically 1:2.1 to 1:3, more specifically 1:2.1 to 1:2.5.

The amount of the supported heterogeneous catalyst used in the reaction will vary, depending on the type of catalyst, its activity, the desired time for the reaction, and like considerations. In general, the amount of the supported heterogeneous catalyst (which includes the support) is 10 to 30 wt. %, specifically 12 to 25 wt. %, more specifically 15 to 20 wt. %, based on the weight of phenolic compound and the phthalic anhydride compound.

The promoter is present in an amount of up to 6 mol %, more specifically, 0.05 to 5 mol %, based on the moles of phthalic anhydride. Specifically, chlorosulphonic acid is present in an amount of 0.05 to 0.5 molar equivalents, more specifically 0.1 to 0.3 molar equivalents, with respect to the phthalic anhydride compound.

The conditions for the reaction vary, depending on the particular phenolic compound, phthalic anhydride compound, supported heterogeneous catalyst, and promoter. In one embodiment, the reaction is conducted at an elevated temperature, for example a temperature of 90° C. to 175° C., specifically 100 to 175° C., more specifically 110 to 165° C., for a reaction time of 10 to 100 hours, specifically 20 to 70 hours, more specifically 30 to 60 hours. The progress of the reaction can be followed by numerous analytical techniques such as gas chromatography or high-pressure liquid chromatography (HPLC).

Following reaction, the reaction mixture comprising the product phenolphthalein compound is typically quenched. Quenching is done, for example, by the addition of a protic organic solvent such as methanol.

The phenolphthalein compound is isolated from the reaction mixture or quenched reaction mixture. In one embodiment, the phenolphthalein compound is isolated by the addition of a solvent in which the phenolphthalein compound is soluble, in an amount effective to dissolve the phenolphthalein compound. The supported heterogeneous catalyst is separated from this mixture, for example by filtering or centrifugation. The filtrate or supernatant is then treated to remove the solvent, for example by distilling the methanol to provide a residue comprising the phenolphthalein compound.

The residue is then heated with a non-polar solvent, for example toluene, to precipitate the crude phenolphthalein compound. The crude phenolphthalein product is then isolated by, for example, filtration, and washing with water or other solvent. The phenolphthalein compound after this step is obtained at a purity of 80 wt. % or greater, specifically 85 to 95 wt. %, more specifically 90 to 95 wt. %, based on the total weight of crude phenolphthalein product (reaction product obtained after removal of the heterogeneous catalyst, precipitation with a non-polar solvent, and washing of the reaction product with water or other solvent). The phenolphthalein compound is obtained in a molar yield of greater than or equal to 70%, specifically greater than 80% yield, based on the moles of phthalic anhydride compound. In one embodiment, the phenolphthalein compound is obtained both at a purity of greater than 80 wt. %, specifically 90 to 99 wt. %, more specifically 94 to 97 wt. %, based on the total weight of crude phenolphthalein product, and in a molar yield of greater than or equal to 70%, specifically greater than 80% yield, based on the moles of phthalic anhydride compound.

In a particularly advantageous embodiment, the supported heterogeneous catalyst is regenerated after the reaction, and reused. Specifically, the supported heterogeneous catalyst is separated from the reaction mixture comprising the phenolphthalein compound, regenerated, and reused for at least one more cycle, for a total of 2 to 4 cycles, specifically 2 to 3 cycles, wherein the first use of the fresh catalyst is considered a first cycle. Without being bound by theory, it is believed that the regeneration removes organic reaction residues that adhere to the catalyst and adversely affect its activity.

In one embodiment, the supported heterogeneous catalyst is regenerated by calcination at an elevated temperature, for example 400 to 900° C., specifically 450 to 750° C., more specifically at 450 to 550° C. for about 8 hours. Calcination is carried out in inert atmosphere.

All or part of foregoing process can be conducted as a batch or continuous process. The ease of separating the catalyst and its regeneration allows for a continuous process.

In a batch process, the reactants are stirred in the presence of the supported heterogeneous catalyst. In a continuous process, the reactants are continuously introduced into at least one reactor comprising a fixed bed or fluidized bed packing comprising the supported catalyst at an appropriate temperature. For example, a continuous process is carried out in a single reactor packed with the supported heterogeneous catalyst, wherein the phenolic compound is passed continuously into the reactor and the phthalic anhydride compound is selectively introduced in one or more stages of the reactor. In other embodiments of a continuous process, a single or multiple reactor system comprising fixed bed packing of the supported heterogeneous catalyst further comprises packing structures designed to alleviate the hydraulic stress that generally results from prolonged operation. Such packing structures assume a variety of structures designed to withstand hydraulic stress, and can comprise materials inert to the reactive materials.

The supported heterogeneous catalysts and methods described herein provide several significant advantages. The supported heterogeneous catalysts provide excellent selectivity and yield, comparable to that obtained by the use of a catalyst system comprising zinc chloride. It is environmentally superior to the use of zinc chloride, since it reduces the effluent disposal problem. After completion of the reaction, the catalyst can be readily separated from the reaction mixture, for example by simple filtration. The catalyst is regenerated and reused for at least one more reaction cycle. The original unused ("native") activity is readily obtained, for example, by washing with solvent or calcination. The catalyst system enables operation in a continuous mode on an industrial scale.

The phenolphthalein compound is used as a starting material to make a wide range of products. For example, the phenolphthalein compound wherein each $R^1$ and $R^2$ are hydrogen is converted to PPPBP by known methods, and then used as a monomer used in the manufacture of homopolycarbonates and copolycarbonates. Such polycarbonates exhibit high transparency, high glass transition temperatures, and other advantageous properties.

The above-described processes are further illustrated by the following non-limiting examples.

EXAMPLES

Preparation of Silicotungstic Acid/Zirconia

Silicotungstic acid supported on zirconia ($H_4SiW_{12}O_{40} \cdot nH_2O/ZrO_2$) was prepared by wet impregnation, using zirconium oxyhydroxide ($ZrO(OH)_x$) as the precursor. The zirconium oxyhydroxide was prepared by dissolving 50 g of $ZrOCl_2 \cdot 8H_2O$ in 1 L of distilled water. To this solution, aqueous ammonia was added slowly with stirring to precipitate the zirconium oxyhydroxide. Ammonia was added slightly in excess (until the smell of ammonia persisted) to ensure complete precipitation. The precipitate was filtered, washed until free from chloride (determined by testing the filtrate with $AgNO_3$), dried at 120° C. for 12 hours, powdered, and then dried for another 12 hours. Approximately 20 g of the zirconium oxyhydroxide was obtained.

To form the supported catalyst, 3 g of silicotungstic acid (SD Fine Chemicals (India)) was added to 100 mL of distilled water. This solution was stirred for 30 min. Then, 20 g of the zirconium oxyhydroxide was added to the solution and the mixture was stirred for 24 hours. Excess water was removed using a rotary evaporator. The mixture was then dried in an oven at 120° C. for 12 hours, well powdered, again dried for 12 hours, and calcined with heating at a rate of 5° C./min to 750° C. for 4 hours. The supported catalyst was then cooled at the same rate to room temperature. Approximately 20 g of the resulting product, a supported catalyst containing 15 wt. % of silicotungstic acid on zirconia, was obtained.

Preparation of Tungstophosphoric Acid/Zirconia.

Tungstophosphoric acid supported on zirconia ($H_3PW_{12}O_{40} \cdot nH_2O/ZrO_2$) was prepared by wet impregnation, using zirconium oxyhydroxide as a precursor for the support. The zirconium oxyhydroxide was prepared by dissolving 50 g of $ZrOCl_2 \cdot 8H_2O$ in 1 L of distilled water. To this solution, aqueous ammonia was added slowly with stirring to precipitate the zirconium oxyhydroxide. Ammonia was added slightly in excess (until the smell of ammonia persisted) to ensure complete precipitation. The precipitate was filtered, washed until free from chloride (determined by testing the filtrate with $AgNO_3$), dried at 120° C. for 12 hours, powdered, and then dried for another 12 hours. Approximately 20 g of the zirconium oxyhydroxide was obtained.

To form the supported catalyst, 3 g of tungstophosphoric acid (TPA) was added to 100 mL of distilled water. This solution was stirred for 30 min. Then, 20 g of the previously prepared $ZrO(OH)_x$, was added to the solution and the mixture was stirred for 24 hours. Excess water was then removed using a rotary evaporator, the resulting mixture was dried in an oven at 120° C. for 12 hours, well powdered, and again dried for 12 hours. The product was then calcined with heating at a rate of 5° C./min to 730° C. for 4 hours and subsequently cooled at the same rate to room temperature. Approximately 20 g of the resulting product, a supported catalyst containing 15 wt. % of tungstophosphoric acid supported on zirconia was obtained.

Preparation of Tungstophosphoric Acid/Titania.

Tungstophosphoric acid on a titania support ($H_3PW_{12}O_{40} \cdot nH_2O/TiO_2$) was prepared by wet impregnation, using tungstophosphoric acid as a tungsten source and titanium oxyhydroxide ($Ti(OH)_x$) as a precursor for the support. The titanium oxyhydroxide was prepared by hydrolysis of 250 mL of titanium (IV) butoxide or titanium (IV) isopropoxide in 1 L of distilled water. The precipitate obtained was filtered and washed, then dried at 120° C. for 12 hours, powdered, and dried for another 12 hours. Approximately 20 g of solid titanium oxyhydroxide was obtained.

To form the supported catalyst, 3 g amount of tungstophosphoric acid was added to 100 mL of methanol. This solution was stirred for 30 min. Then, 20 g of the previously prepared titanium oxyhydroxide was added to the solution and the mixture was stirred for 24 hours. Excess methanol was then removed using a rotary evaporator, the resulting mixture was dried in an oven at 120° C. for 12 hours, well powdered, and again dried for 12 hours. The product was calcined with heating at a rate of 5° C./min to 730° C. for 4 hours and then cooled at the same rate to room temperature. Approximately 20 g of the resulting product, a supported catalyst containing 15 wt. % of tungstophosphoric acid supported on titania, was obtained.

Preparation of Tungstophosphoric Acid on Zirconia-Doped Zeolite.

Tungstophosphoric acid on a zirconia-doped SBA-15 zeolite was prepared by impregnating the zeolite with a zirconia precursor, followed by impregnation with the tungstophosphoric acid.

To prepare the SBA-15 zeolite, 4 g of a template (polyethylene glycol-polypropylene glycol-polyethylene glycol, MW=5,800) was placed in a polypropylene bottle. Then, 30 mL of distilled water was added, the mixture was stirred for 4 hours, followed by the addition of 120 g of a 2 M HCl solution, followed by stirring for another 2 hours. Subsequently, 8.54 g of a $C_1$-$C_6$ alkyl-substituted orthosilicate (tetraethyl orthosilicate), was added dropwise to the homogeneous solution with stirring. The resulting gel was stirred at 40° C. for 24 hours and finally stored in an oven at 100° C. for 48 hours under static conditions.

The resulting solid was cooled, filtered, washed repeatedly with distilled water, and dried in an air oven at 100° C. for 12 hours. Calcination at 500° C. for 8 hours yielded the SBA-15 zeolite.

The SBA-15 zeolite thus obtained was further calcined in a calcination furnace using a borosilicate Petri dish, to yield about 2.5 g of SBA-15 zeolite, employing the following heating program.

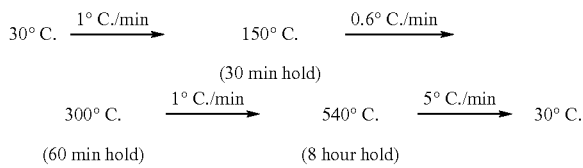

The zeolite was impregnated with zirconia by first adding 5.86 g of $ZrOCl_2 \cdot 8H_2O$ to 200 mL of distilled water. This solution was stirred for 30 min. Then, 10 g of the SBA-15 zeolite (prepared as described above, from multiple batches) was added to the solution, and the mixture was stirred for 3 hours. The excess water was removed using a rotary evaporator and the resulting mixture was then dried in an oven at 110° C. for 14 hours to yield about 13 g of the zeolite containing about 22.4 wt. % of zirconia.

To make the supported heterogeneous catalyst, 0.29 g of tungstophosphoric acid was added to 195 mL of distilled water. This solution was stirred for 30 min and 13.70 g of the above-prepared zirconia-doped zeolite (from multiple batches) was added to the solution and the mixture was stirred for 3 hours. The excess water was evaporated in a rotary evaporator, and the resulting mixture was then dried in an oven at 110° C. for 14 hours. The dried mixture was then calcined with a heating rate of 5° C./min to 850° C. for 4 hours and cooled with a cooling rate of 5° C./min to room temperature. About 11 g of the resulting supported heterogeneous catalyst was obtained.

Methods of Analysis.

In order to measure the progress of the reactions in the following experiments, HPLC analysis was carried out by using a solution of about 25 milligrams of a sample from the reaction mixture dissolved in about 50 milliliters of acetonitrile:0.05% aqueous $H_3PO_4$ (70:30, v:v) The HPLC instrument was equipped with a C-8 (reverse phase) column maintained at a temperature of 40° C., and an ultraviolet detector capable of detecting components at a wavelength of 225 nanometers. A solvent mixture of acetonitrile and water with 0.02% $H_3PO_4$ of gradient elution was used. The flow rate was maintained at 1 milliliter per minute. Area percent purity was computed from the area value for each peak detected in the chromatogram divided by the total area from all peaks detected. To measure weight percent, calibration curves for phenol, phthalic anhydride, and phenolphthalein were first generated. Then the weight percent of a given component in a sample was calculated using these calibration curves.

The weight percent assay of isolated solid phenolphthalein (PP) was computed by calculating the phenol and phthalic anhydride content using suitable calibration graphs, and all other impurities were calculated using the response factor of PP. The purity of PP was calculated by subtracting the amount of phenol, phthalic anhydride, and "others" from 100. In the Tables 2 and 3 below, the HPLC data for phthalic anhydride (PA) and phenol is in area % and the isolated solid PP is in wt. %.

X-ray diffraction patterns were obtained on a Bruker small angle X-ray scattering (SAXS) instrument with general area detector diffraction using Cu Kα radiation with a 2θ step size of 0.01°. SAXS pattern of the samples was collected in reflection mode using a Rigaku $D_{max}$ 2500 diffractometer equipped with Ni filtered Cu radiation.

Example 1

Preparation of Phenolphthalein

In a 250-ml round bottom flask equipped with mechanical stirrer, thermometer, nitrogen inlet and reflux condenser, 18.5 g of phthalic anhydride and 27.6 g of phenol were charged, followed by 10.0 g of supported heteropolyacid catalyst (silicotungstic acid in Sample 1) and 1.9 g chlorosulphonic acid, while maintaining the round bottom flask in a nitrogen atmosphere at 50 to 60° C. This amounted to 1 molar equivalent of phenolphthalein, 2.25 molar equivalents of phenol with respect to the phthalic anhydride, and 17% by weight loading of the catalyst.

The reaction mixture was then heated with stirring at 140° C. (bath temperature). During the course of the reaction for 48 hours, the reaction mass progressively turned from orange to brownish orange to deep brown. The reaction product was then quenched with a solvent, 160 mL of methanol. The quenched mass comprising phenolphthalein, unreacted phthalic anhydride, and by-products was stirred at 85° C. for about 30 min. The solution was then filtered to remove solid catalyst as a residue and to obtain a filtrate containing the phenolphthalein. The methanol was removed from the filtrate using a Rotovac® evaporator, and the viscous mass was then heated with 160 mL of toluene, and stirred at 85° C. for 30 min. The precipitated solid (precipitated phenolphthalein) was filtered while hot and washed with hot water. The resulting brownish yellow solid was dried under vacuum at 100° C. overnight to obtain crude phenolphthalein. The yield of crude phenolphthalein was 35.0 g (88% by weight of the crude phenolphthalein). The purity was 95.88%, as determined by HPLC.

Phenolphthalein was also prepared using the above procedure and 15 wt. tungstophosphoric acid/zirconia, 15 wt. % tungstophosphoric acid/titania, and 15 wt. % wt. % tungstophosphoric acid/22.4 wt. % $ZrO_2$ on 62.6 wt. % SBA-15 zeolite. The results are shown in Table 1.

TABLE 1

| Sample No. | Catalyst Composition | Reaction Time/ Temperature | Conversion (mole % PA) | Reaction Yield (wt. %) | Isolated Yield (mole %) | Purity (wt. %) |
|---|---|---|---|---|---|---|
| 1 | 15 wt. % silicotungstic acid/zirconia | 165° C. 30 hours | 88.3 | 46.5 | 62.0 | 76.7 |
| 2 | 15 wt. % tungstophosphoric acid/zirconia | 165° C. 30 hours | 97.9 | 53.1 | 68.0 | 75.9 |
| 3 | 15 wt. % tungstophosphoric acid/titania | 165° C. 30 hours | 97.7 | 37.9 | 50.0 | 84.0 |
| 4 | 15 wt. % tungstophosphoric acid/22.4 wt. % $ZrO_2$ on 62.6% SBA-15 | 140° C. 48 hours | 91.4 | 68.4 | 75.5 | 91.3 |

The results in Table 1 show that a high purity phenolphthalein product can be obtained at good yield using the catalysts described herein.

Example 2

To demonstrate regeneration of the supported catalyst, phenolphthalein was prepared using 15 wt. % silicotungstic acid/zirconia as the supported catalyst, as in Sample 1 of Example 1, with 1 molar equivalent of phthalic anhydride to 2.25 molar equivalent of phenol with respect to the phthalic anhydride. The temperature of the reaction was 165° C., and the reaction time was 30 hours.

The product was isolated by quenching the reaction with methanol, filtering the catalyst, and removing the methanol by distillation. The residue was heated with toluene at 80° C. to obtain a solid that was filtered, washed with hot water, and dried. The used catalyst was obtained as a residue from the first filtering step. The catalyst was regenerated by calcination at 500° C. for 8 hours using a heating and cooling rate of 5°

C./minute. The regenerated catalyst was then used to make phenolphthalein as described in Example 1.

The results shown in Table 2 show the progress of the reaction using fresh 15 wt. % silicotungstic acid/zirconia, based on HPLC measurements.

TABLE 2

| Time (hours) | Phthalic Anhydride (area %) | Phenol (area %) | Purity of Phenolphthalein (wt. %) |
|---|---|---|---|
| 16 | 15.3 | 16.97 | 45.75 |
| 24 | 14.0 | 15.10 | 46.37 |
| 30 | 11.7 | 15.10 | 46.50 |
| Isolated Phenolphthalein | 1.9 | 1.39 | 76.68 |

The results shown in Table 2 show the progress of the reaction using the regenerated 15 wt. % silicotungstic acid/zirconia, based on HPLC measurements.

TABLE 3

| Time (hours) | Phthalic Anhydride (area %) | Phenol (area %) | Purity of Phenolphthalein (wt. %) |
|---|---|---|---|
| 3 | 21.5 | 17.9 | 43.08 |
| 19 | 8.8 | 9.2 | 52.33 |
| 22 | 8.4 | 9.0 | 51.93 |
| 30 | 6.8 | 9.3 | 48.07 |
| Isolated Phenolphthalein | NA | NA | 85.80 |

A yield of 60.00% and a purity of isolated phenolphthalein of 85.80% for the regenerated catalyst were obtained, compared to a yield of 62% and a purity of isolated phenolphthalein of 76.68% for the fresh catalyst.

Similar testing was conducted for the other supported catalysts, and the results shown in Table 4.

calcination temperatures during preparation; (B) a porous support and a heteropolyacid, after being subjected to different calcination temperatures during preparation; and (C) a porous support and varying amounts of a heteropolyacid, after being subjected to calcination.

In particular, a zirconia support with no heteropolyacid was calcined at different temperatures: (a) 120° C., (b) 250° C., (c) 350° C., (d) 450° C., (e) 550° C., (f) 650° C., and (g) 750° C., and subjected to XRD analysis, which are shown in FIG. 1A. The peaks labeled "M" correspond to the monoclinic form of zirconia, while the peaks labeled "T" correspond to the tetragonal form of zirconia. It is apparent that at higher calcination temperatures, the M peaks are more intense than the T peaks. In comparison, when 15 wt. % silicotungstic acid/zirconia was calcined at temperatures of (a) 120° C., (b) 250° C., (c) 350° C., (d) 450° C., (e) 550° C., (f) 650° C., and (g) 700° C., (h) 750° C., (i) 800° C., and (j) 850° C., at higher calcination temperatures the zirconia showed an increase in the tetragonal form, compared to the monoclinic form as shown in FIG. 1B. Without wishing to be bound by theory, it is believed that the tungsten-containing heteropolyacid delayed the crystallization of zirconia from zirconium oxyhydroxide and stabilized the tetragonal form of zirconia.

FIG. 1C shows the XRD analysis of silicotungstic acid/zirconia, calcined at 750° C., at various loadings of silicotungstic acid. Formation of bulk $WO_3$ was observed a loading of silicotungstic acid of greater than 15 wt. %, i.e., decomposition of silicotungstic acid was observed beginning at a calcination temperature of about 750° C.

Figure 2:
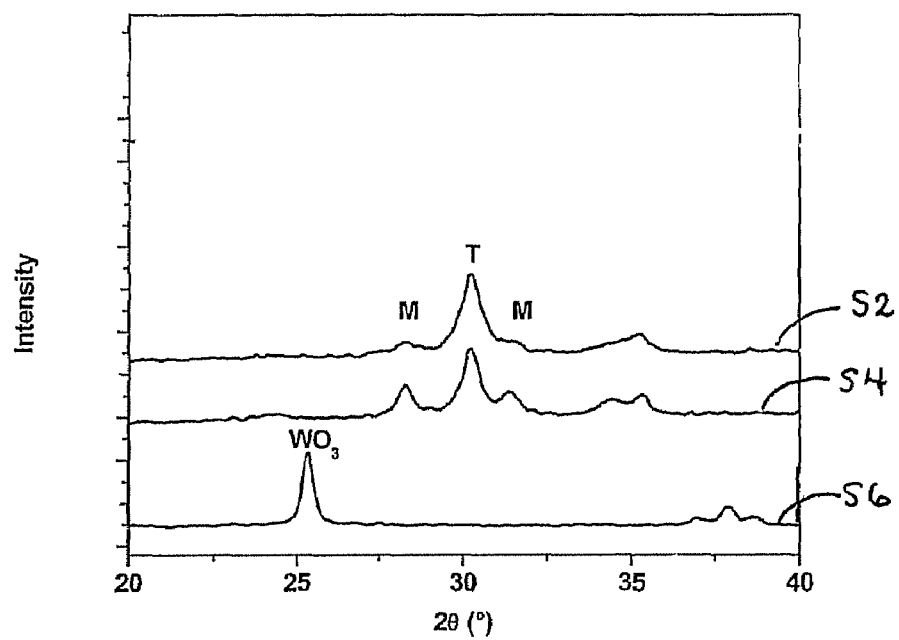
FIG. 2 shows X-ray diffraction patterns, according to Example 3, for various heterogeneous catalysts (Sample 2 (S2); Sample 4 (S4); and Sample 6 (S6)) after being used for preparing phenolphthalein and then being regenerated by calcination.

FIG. 2 shows the XRD patterns of recycled zirconia-supported catalysts, in particular, the catalysts of Sample 2, Sample 4, and Sample 6 in Table 4, regenerated by calcination after use in the preparation of phenolphthalein. The XRD analysis showed that regeneration resulted in a dominant, i.e., comparatively more intense, tetragonal (T) phase crystal structure compared to the monoclinic (M) phase crystal phase.

TABLE 4

| Sample No. | Catalyst Composition | Cycle | Method of Regeneration | Conversion (mole % PA) | Reaction Yield (wt. %) | Isolated Yield (mole %) | Purity (wt. %) |
|---|---|---|---|---|---|---|---|
| 1 | 15 wt. % silicotungstic acid/zirconia | Fresh | None | 88.3 | 46.5 | 62 | 76.7 |
| 2 | 15 wt. % silicotungstic acid/zirconia | Recycled Once | Calcined at 500° C. for 8 hours | 93.2 | 48.1 | 60.0 | 85.8 |
| 3 | 15 wt. % tungstophosphoric acid/zirconia | Fresh | None | 97.9 | 53.1 | 68.0 | 75.9 |
| 4 | 15 wt. % tungstophosphoric acid/zirconia | Recycled Once | Calcined at 500° C. for 8 hours | 87.4 | 43.5 | 65.0 | 91.6 |
| 5 | 15 wt. % tungstophosphoric acid/titania | Fresh | None | 97.7 | 37.9 | 50.0 | 84.0 |
| 6 | 15 wt. % tungstophosphoric acid/titania | Recycled Once | Calcined at 500° C. for 8 hours | NA | NA | 50.0 | 83.1 |

NA (data not available)

Example 3

Various supported heteropolyacid catalysts were analyzed by XRD analysis. FIGS. 1A, 1B, and 1C show X-ray diffraction patterns, for: (A) a porous support without using a heteropolyacid composition, after being subjected to different The singular forms "a," "an," and "the" include plural referents unless the context clearly dictates otherwise. Unless defined otherwise, technical and scientific terms used herein have the same meaning as is commonly understood by one of skill in the art to which this invention belongs. The endpoints of all ranges directed to the same component or property are inclusive of the endpoint and independently combinable (e.g., ranges of "less than or equal to about 25 wt. %, or, more specifically, about 5 wt. % to about 20 wt. %," is inclusive of the endpoints and all intermediate values of the ranges of "about 5 wt. % to about 25 wt. %," etc.).

Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group.

As used herein, the term "hydrocarbyl" is defined as a monovalent moiety formed by removing a hydrogen atom from a hydrocarbon. Representative hydrocarbyls are alkyl groups having 1 to 12 carbon atoms, such as methyl, ethyl, propyl, butyl, pentyl, hexyl, heptyl, octyl, nonyl, undecyl, decyl, dodecyl, and the isomeric forms thereof; aryl groups having 6 to 12 carbon atoms, such as ring-substituted and ring-unsubstituted forms of phenyl, tolyl, xylyl, naphthyl, biphenyl, and the like; arylalkyl groups having 7 to 12 carbon atoms, such as ring-substituted and ring-unsubstituted forms of benzyl, phenethyl, phenpropyl, phenbutyl, and the like; and cycloalkyl groups, such as cyclopropyl, cyclobutyl, cyclopentyl, cyclohexyl, cycloheptyl, cyclooctyl, and the like, as well as the corresponding oxides of the foregoing groups. The term "aryl" as used herein refers to an aromatic monovalent group containing only carbon in the aromatic ring or rings.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

While various embodiments have been set forth for the purpose of illustration, the foregoing descriptions should not be deemed to be a limitation on the scope herein. Accordingly, various modifications, adaptations, and alternatives can occur to one skilled in the art without departing from the spirit and scope herein.

The invention claimed is:

1. A method for producing a phenolphthalein compound comprising:

reacting a phenolic compound of the formula:

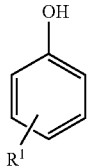

wherein $R^1$ is a hydrogen or a $C_1$-$C_{12}$ hydrocarbyl group, with a phthalic anhydride compound of the formula:

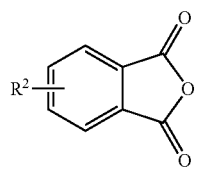

wherein $R^2$ is a hydrogen, a $C_1$-$C_{12}$ hydrocarbyl group, or a halogen, in the presence of a heterogeneous catalyst and a promoter to form a reaction mixture comprising a phenolphthalein compound of the formula:

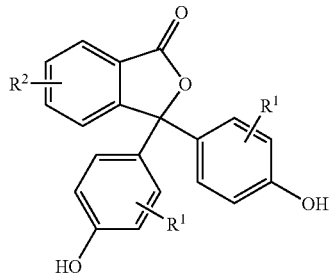

wherein each $R^1$ is independently a hydrogen or a $C_1$-$C_{12}$ hydrocarbyl group; and $R^2$ is a hydrogen, a $C_1$-$C_{12}$ hydrocarbyl group, or a halogen;
wherein the heterogeneous catalyst comprises, on a porous support, a calcination product of a heteropolyacid composition.

2. The method of claim 1 wherein the heteropolyacid composition comprises molybdenum, tungsten, vanadium, or a combination comprising at least one of the foregoing metals.

3. The method of claim 1 wherein the heteropolyacid composition comprises a compound, or structural units derived therefrom, of the formula:

$$(H)_n(M^4)(M^5)_{12}O_{40}$$

wherein the subscript n is 3, 4, 5, or 6, $M^4$ is phosphorus or silicon, and $M^5$ is tungsten, molybdenum, or a combination comprising at least one of the foregoing metals.

4. The method of claim 3 wherein the heteropolyacid is silicotungstic acid, tungstophosphoric acid, molybdophosphoric acid, or a combination comprising at least one of the foregoing heteropolyacids.

5. The method of claim 1 wherein the porous support is zirconium oxide, titanium oxide, cerium oxide, silicon oxide, aluminum oxide, magnesium oxide, niobium oxide, tin oxide, aluminosilicate, or a combination comprising at least one of the foregoing.

6. The method of claim 1 wherein the heteropolyacid composition comprises tungsten and the porous support comprises zirconium oxide.

7. The method of claim 1 wherein the heteropolyacid composition and the porous support are, respectively, silicotungstic acid and zirconia, tungstophosphoric acid and zirconia, tungstophosphoric acid and titania, tungstophosphoric acid and both zirconia and aluminosilicate, or a combination comprising at least one of the foregoing pairs of heteropolyacid composition and porous support.

8. The method of claim 1 wherein the heterogeneous catalyst is the product of a process comprising contacting a solid support precursor with a heteropolyacid composition; and calcining the contacted solid support precursor and heteropolyacid composition to provide the heterogeneous catalyst, wherein the solid support precursor is zirconium oxyhydroxide, titanium hydroxide, a $C_1$-$C_6$ alkyl-substituted substituted orthosilicate, zirconium oxychloride, or a combination comprising at least one of the foregoing solid support precursors.

9. The method of claim 1 wherein the porous support comprises a combination of an aluminosilicate zeolite and zirconium oxide.

10. The method of claim 1 wherein the porous support comprises zirconium oxide.

11. The method of claim 1 wherein the promoter is chlorosulphonic acid, a $C_1$-$C_{12}$ alkyl sulphonic acid, a $C_6$-$C_{12}$ aryl sulphonic acid, a $C_1$-$C_{12}$ alkyl $C_6$-$C_{12}$ aryl sulphonic acid, a halogenated $C_1$-$C_{12}$ alkyl sulphonic acid, a halogenated $C_6$-$C_{12}$ aryl sulphonic acid, a halogenated $C_1$-$C_{12}$ alkyl $C_6$-$C_{12}$ aryl sulphonic acid, trichloroacetic acid, triflic acid, boron trifluoride, or a combination comprising at least one of the foregoing promoters.

12. The method of claim 1 wherein the promoter is chlorosulphonic acid.

13. The method of claim 1 wherein after reacting, the heterogeneous catalyst is separated from the reaction mixture, then regenerated.

14. The method of claim 13 wherein the heterogeneous catalyst is used in a total of two to four cycles of reaction in a batch process.

15. The method of claim 13, wherein the heterogeneous supported catalyst is regenerated by calcination at a temperature of 400 to 900° C.

16. The method of claim 1, wherein the method further comprises:
quenching the reaction mixture comprising the phenolphthalein compound with a first organic solvent in which the phenolphthalein compound dissolves to provide a first quenched reaction mixture;
filtering the first quenched reaction mixture to provide a solid residue comprising the heterogeneous catalyst and a filtrate comprising the organic solvent and the phenolphthalein compound.

17. The method of claim 16, further comprising regenerating the heterogeneous catalyst in the solid residue.

18. The method of claim 16, further comprising
removing the first organic solvent from the filtrate to provide a residue comprising the phenolphthalein compound and
heating the residue with a second, non-polar organic solvent to provide a precipitate comprising the phenolphthalein compound, wherein the phenolphthalein compound in the precipitate has a purity of greater than or equal to 80 weight percent, based on the weight of the precipitate, and the phenolphthalein compound is obtained in a yield of greater than or equal to 70 mole percent, based on the moles of the phthalic anhydride compound.

19. A method for producing a phenolphthalein compound comprising:
reacting a phenolic compound of the formula:

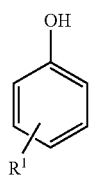

wherein $R^1$ is a hydrogen or a $C_1$-$C_{12}$ hydrocarbyl group, with a phthalic anhydride compound of the formula:

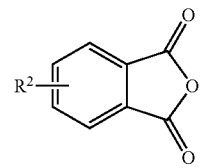

wherein $R^2$ is a hydrogen, a $C_1$-$C_{12}$ hydrocarbyl group, or a halogen, in the presence of a heterogeneous catalyst and a promoter to form a reaction mixture comprising a phenolphthalein compound of the formula:

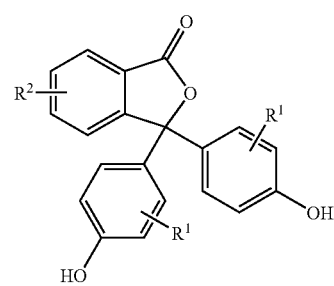

wherein each $R^1$ is independently a hydrogen or a $C_1$-$C_{12}$ hydrocarbyl group; and $R^2$ is a hydrogen, a $C_1$-$C_{12}$ hydrocarbyl group, or a halogen;
wherein the heterogeneous catalyst comprises, on a porous support, a calcination product of an oxygen-containing inorganic heteropolyacid comprising a polyatom selected from the group consisting of molybdenum, tungsten, vanadium, niobium, or a combination thereof, and a central heteroatom selected from the group consisting of phosphorous, silicon, germanium, boron, cobalt, and a combination thereof.

20. A method for producing a phenolphthalein, comprising:
reacting a phenolic compound of the formula:

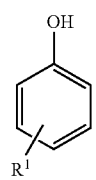

wherein $R^1$ is a hydrogen, with a phthalic anhydride compound of the formula:

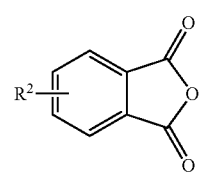

wherein $R^2$ is a hydrogen, a $C_1$-$C_{12}$ hydrocarbyl group, or a halogen, in the presence of a heterogeneous catalyst and a promoter to form a reaction mixture comprising a phenolphthalein compound of the formula:

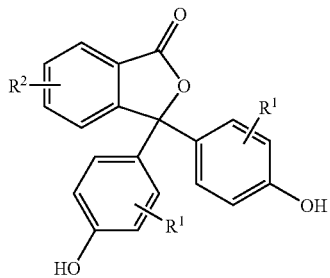

wherein each $R^1$ is a hydrogen, and $R^2$ is a hydrogen, a $C_1$-$C_{12}$ hydrocarbyl group, or a halogen; wherein the heterogeneous catalyst comprises, on a porous support, a calcination product of a heteropolyacid composition that comprises a compound, or structural units derived from the compound, of the formula:

$$(H)_n(M^4)(M^5)_{12}O_{40}$$

wherein the subscript n is 3 or 4, $M^4$ is phosphorus or silicon, and $M^5$ is tungsten, molybdenum, or a combination comprising at least one of the foregoing metals;
quenching the reaction mixture comprising the phenolphthalein compound with a first organic solvent in which the phenolphthalein compound dissolves to provide a first quenched reaction mixture comprising dissolved phenolphthalein compound;
filtering the first quenched reaction mixture to provide a solid residue comprising the heterogeneous catalyst and a filtrate comprising the organic solvent and the phenolphthalein compound;
removing the organic solvent from the filtrate to provide a residue comprising the phenolphthalein compound; and
regenerating the heterogeneous supported catalyst.

* * * * *